United States Patent
Popple

(10) Patent No.: US 10,220,222 B2
(45) Date of Patent: Mar. 5, 2019

(54) SYSTEMS AND METHODS FOR PROVIDING RADIOTHERAPY TREATMENT

(71) Applicant: THE UAB RESEARCH FOUNDATION, Birmingham, AL (US)

(72) Inventor: Richard Popple, Homewood, AL (US)

(73) Assignee: UAB RESEARCH FOUNDATION, Birmingham, AL (US)

(*) Notice: Subject to any disclaimer, the term of this patent is extended or adjusted under 35 U.S.C. 154(b) by 207 days.

(21) Appl. No.: 15/320,043

(22) PCT Filed: Jul. 16, 2015

(86) PCT No.: PCT/US2015/040814
§ 371 (c)(1),
(2) Date: Dec. 19, 2016

(87) PCT Pub. No.: WO2016/011300
PCT Pub. Date: Jan. 21, 2016

(65) Prior Publication Data
US 2017/0197094 A1  Jul. 13, 2017

Related U.S. Application Data

(60) Provisional application No. 62/025,165, filed on Jul. 16, 2014.

(51) Int. Cl.
*A61N 5/10* (2006.01)

(52) U.S. Cl.
CPC ......... *A61N 5/1047* (2013.01); *A61N 5/1039* (2013.01); *A61N 5/1045* (2013.01); *A61N 5/1081* (2013.01)

(58) Field of Classification Search
CPC .. A61N 5/1045; A61N 5/1081; A61N 5/1039; A61N 5/1047; A61N 2005/1087;
(Continued)

(56) References Cited

U.S. PATENT DOCUMENTS

| | | |
|---|---|---|
| 4,868,843 A | 9/1989 | Nunan |
| 5,012,506 A | 4/1991 | Span et al. |

(Continued)

OTHER PUBLICATIONS

Extended European Search Report, Application No. 15822567.2, dated Feb. 13, 2018.
(Continued)

*Primary Examiner* — Don Wong
(74) *Attorney, Agent, or Firm* — Thomas Horstemeyer, LLP; Christopher B. Linder; Jason M. Perilla

(57) ABSTRACT

In one embodiment, radiotherapy treatment is provided to a target volume of a patient by configuring a multileaf collimator of a radiation treatment machine in a first orientation so as to form an actual aperture having a first orientation, delivering radiation to the target volume through the actual aperture while in the first orientation with a single pass along an arcuate path centered on the target volume, configuring the multileaf collimator in a second orientation so as to place the actual aperture in a second orientation that is different from the first orientation, and delivering radiation to the target volume through the actual aperture while in the second orientation with a single pass back along the arcuate path such that a relatively large cumulative dose of radiation is delivered to the target volume through a virtual aperture created by an area of overlap between the first and second actual aperture orientations.

18 Claims, 5 Drawing Sheets

(58) Field of Classification Search
CPC .... A61N 2005/1043; A61N 2005/1098; A61N 5/1077
See application file for complete search history.

(56) References Cited

U.S. PATENT DOCUMENTS

| | | | |
|---|---|---|---|
| 5,818,902 A | 10/1998 | Yu | |
| 6,240,161 B1 | 5/2001 | Siochi | |
| 6,813,336 B1 | 11/2004 | Siochi | |
| 9,962,560 B2 * | 5/2018 | Zwart | .................. A61N 5/1043 |
| 2006/0231775 A1 | 10/2006 | Harada | |
| 2011/0091015 A1 | 4/2011 | Yu | |
| 2013/0150646 A1 | 6/2013 | Scholz | |

OTHER PUBLICATIONS

International Search Report for PCT/US2015/040814 dated Oct. 16, 2015.

* cited by examiner

SYSTEMS AND METHODS FOR PROVIDING RADIOTHERAPY TREATMENT

CROSS-REFERENCE TO RELATED APPLICATION

This application is the 35 U.S.C. § 371 national stage application of PCT Application No. PCT/US2015/040814, filed Jul. 16, 2015, where the PCT claims priority to U.S. Provisional Application Ser. No. 62/025,165, filed Jul. 16, 2014, both of which are hereby incorporated by reference herein in their entireties.

BACKGROUND

Radiation therapy, or radiotherapy, uses high-energy radiation to destroy target cells. In external-beam radiation therapy, photon beams emitted by radiation treatment machine, such as a linear accelerator, are focused on a target volume within the body. Circular collimators, often referred to as "cones," have been used to limit the breadth of the radiation emitted by the linear accelerator so as to limit the radiation exposure of non-targeted patient tissue. Such cones are normally attached to the linear accelerator immediately prior to radiotherapy treatment. Testing is required to ensure that the cone is aligned with the target volume with high accuracy. In addition, the linear accelerator must be properly configured to use the cone. Unfortunately, such testing and configuring is time consuming and errors in these processes can result in the misadministration of radiation to the patient.

Later model linear accelerators are typically equipped with built-in multileaf collimators (MLCs) that ameliorate the problems of cones and their use. MLCs comprise many thin "leaves" of a high atomic numbered material, such as tungsten, that can be independently linearly moved into and out of the path of a radiation beam in order to block it. Accordingly, MLCs can be used to conformally shape radiotherapy treatment beams.

While MLCs overcome the drawbacks of cones, the resolution of an MLC is typically insufficient for very small target volumes, such as those approximately 5 mm or less in diameter. In addition, configuration of the MLC is typically patient-specific and the calculation and measurement of the resulting dose distribution is complicated and fraught with difficulties that can result in errors.

From the above discussion, it can be appreciated that it would be desirable to have an alternative way to deliver very small radiation dose distributions using a radiation treatment machine equipped with an MLC.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative way to deliver very small radiation dose distributions using a radiation treatment machine equipped with a multileaf collimator (MLC). Disclosed herein are systems and methods for providing radiotherapy treatment that are capable of such delivery. As is described below, stored radiotherapy treatment plans can be selected and used to control operation of a radiation treatment machine, such as a linear accelerator, that is equipped with an MLC. A radiation source of the machine traverses multiple arcuate paths centered on the target volume to which radiation is to be focused. In some embodiments, each arcuate path is traversed twice: a first time with the MLC in a first orientation that forms an aperture having a first orientation, and a second time with the MLC in a second orientation that forms an aperture having a second orientation. The two aperture orientations only partially overlap each other along the arcuate path such that a relatively high dosage of radiation is only delivered through a relatively small "virtual aperture" defined by the intersection of the first and second aperture orientations. The result is the relatively high dosage of radiation being delivered with a resolution greater than that the MLC can provide in a single pass. In some embodiments, the resolution that can be achieved is equivalent to that provided by a small diameter circular collimator, or cone. Accordingly, the MLC can be used in a manner in which it acts as a "virtual cone." In some embodiments, the magnitude of the radiation dose delivered along the arcuate paths can be controlled as a function of the angular position along the paths to more evenly administer the radiation to the patient.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
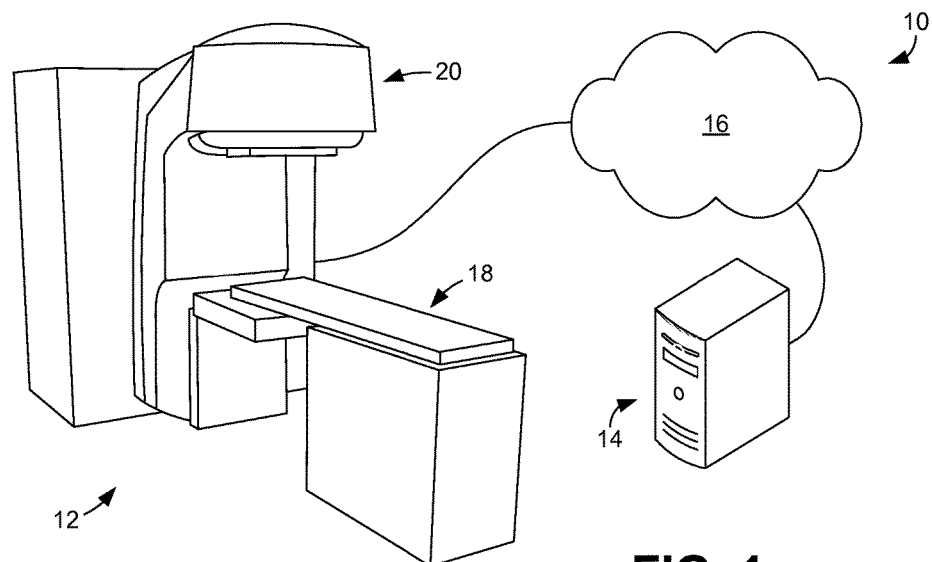
FIG. 1 is an illustration of an embodiment of a radiotherapy treatment system.

FIG. 1 illustrates an example radiotherapy treatment system 10 that can be used to provide radiotherapy treatment to a patient. As shown in the figure, the system 10 generally includes a radiation treatment machine 12, such as a linear accelerator, and a computer 14, which are in electronic communication with each other via a computer network 16. While a separate computer 14 is shown in FIG. 1, it is noted that the functionality of the computer can be integrated into the radiation treatment machine, if desired. The radiation treatment machine 12 comprises a treatment table 18 upon which a patient may lie and a rotatable gantry 20 that can rotate around the table. Provided within the gantry is a radiation source and an MLC that can be used to limit the radiation emitted by the radiation source.

The MLC comprises multiple pairs of opposed leaves that lie within the same plane. The pairs of leaves can be individually linearly displaced toward or away from each other to create the aperture through which the radiation treatment machine's radiation beam will be emitted. The smallest aperture that can be formed by the MLC is an aperture formed when each opposed pair of leaves is closed (i.e., brought into contact or nearly in contact with each other) except for two pairs (two pairs are required to be opened with commercial MLCs to create a symmetric field centered on the machine axis). The width of that aperture is defined by the spacing between those two pairs of leaves, which is adjustable, while the length of the aperture is dictated by the width of the leaves, which is fixed (see discussion of FIG. 5 below). Because the leaf width is fixed, it limits the resolution of the radiation treatment machine 12. In some embodiments, the leaves each have a width of approximately 2.5 mm or greater, in which case the length of the aperture formed by two pairs of leaves can be no smaller than 5 mm long. In cases in which the target volume is very small, such as target volumes having a diameter of around 5 mm, that length dimension is too large. As is described below, this limitation can be overcome through specialized control over the MLC and the radiotherapy treatment process.

Figure 2:
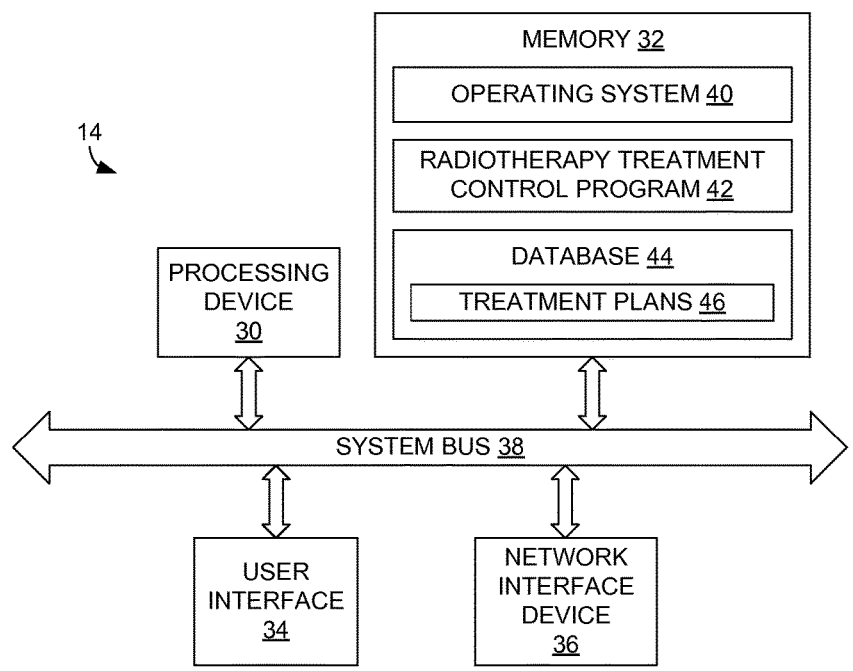
FIG. 2 is a block diagram of a computer shown in FIG. 1.

Referring next to FIG. 2, illustrated is an example configuration for the computer 14 shown in FIG. 1. As indicated in FIG. 2, the computer 14 generally comprises a processing device 30, memory 32, a user interface 34, and a network interface device 36, each of which is connected to a system bus 38. The processing device 30 can include a central processing unit (CPU). The memory 32 includes any one of or a combination of volatile memory elements (e.g., RAM) and nonvolatile memory elements (e.g., hard disk, ROM, Flash, etc.). The user interface 34 comprises the components with which a user interacts with the computer 14, such as a keyboard, keypad, and display screen, and the system bus 38 are adapted to facilitate communications with other devices.

The memory 32 (a non-transitory computer-readable medium) comprises programs (logic) including an operating system 40 and a radiotherapy treatment control program 42 that can be used to control operation of the radiation treatment machine 12 and its provision of radiotherapy treatment to the patient. In addition, the memory 32 comprises a database 44 that can stores predefined radiotherapy treatment plans 46 that can be selected by a user, such as a radiation oncologist or radiation technician.

Figure 3:
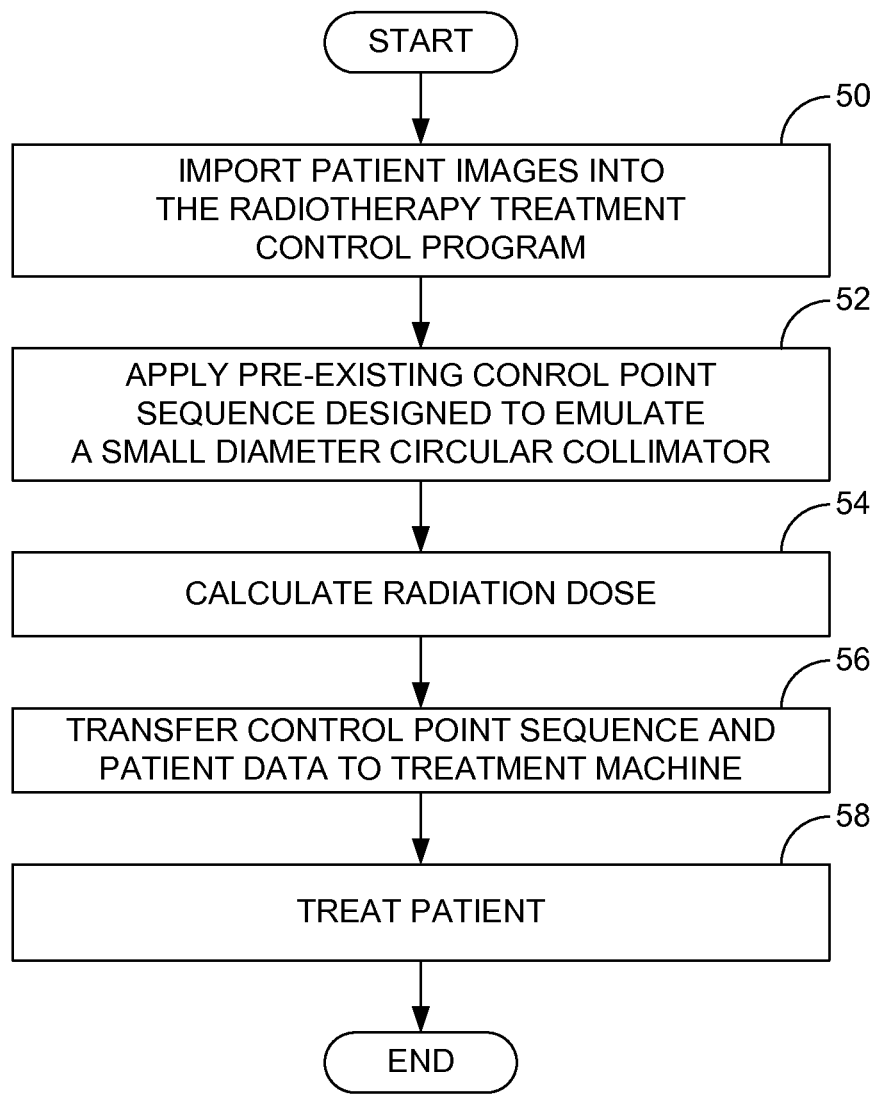
FIG. 3 is a flow diagram of an embodiment of a method for providing radiotherapy treatment to a patient.

FIG. 3 illustrates a method for providing radiotherapy treatment to a patient, which can be performed by system 10 of FIG. 1. In this method it is assumed that the target volume is very small, such as a generally spherical (i.e., a sphere or spheroid) target volume having a diameter in the range of approximately 3 to 7 mm. In some embodiments, the target volume may have a diameter of approximately 5 mm.

Beginning with block 50 of FIG. 3, patient images are imported into the radiotherapy control program 42. The patient images can be any type of images that identify the patient anatomical feature that is to be the target of the radiotherapy. Through such identification, the target volume can be determined. By way of example, the images can comprise computed tomography (CT), magnetic resonance imaging (MRI), positron emission tomography (PET), or ultrasound scans.

With reference next to block 52, a pre-existing control point sequence designed to emulate the results that would be achieved with the radiation treatment machine using a small diameter circular collimator or cone is applied. In other words, the control point sequence is designed to create a "virtual cone" using the radiation treatment machine MLC. In some embodiments, a user of the radiotherapy control program 42 selects an appropriate treatment plan 46 from the database 44 that contains a pre-defined control point sequence. In such cases, the user can select the treatment plan 46 based upon the parameters of the radiotherapy treatment that is to be administered to the patient. Such parameters can include the size of the target volume and the amount of radiation to be delivered to the target volume.

Turning to block 54, the radiotherapy control program 42 calculates the radiation dose that is to be applied to the target volume. Once the dose is calculated, the radiotherapy control program 42 can transfer the control point sequence and patient data to the radiation treatment machine, as indicated in block 56. At this point, the patient can be treated using the radiation treatment machine, as indicated in block 58.

As noted above, the control point sequence provided to the radiation treatment machine controls the machine and its MLC in a way in which radiation is delivered to the patient as if the machine was equipped with a small diameter cone. This result is achieved by delivering radiation through multiple passes along arcuate paths centered on the target volume. More particularly, along each arcuate path, a first pass is made with the MLC in a first orientation in which an aperture having a first orientation is formed, and then a second pass is made with the MLC in a second orientation different from the first in which the aperture has a second orientation. Because the two apertures have different orientations, the only partially overlap each other along the arcuate path. The result is that a relatively larger dose of radiation is emitted through the overlapping area, i.e., a "virtual aperture," which has a length that is smaller than the lengths of the actual aperture. Accordingly, that radiation is delivered with a resolution that exceeds that which the MLC can provide in a single pass.

Figure 4:
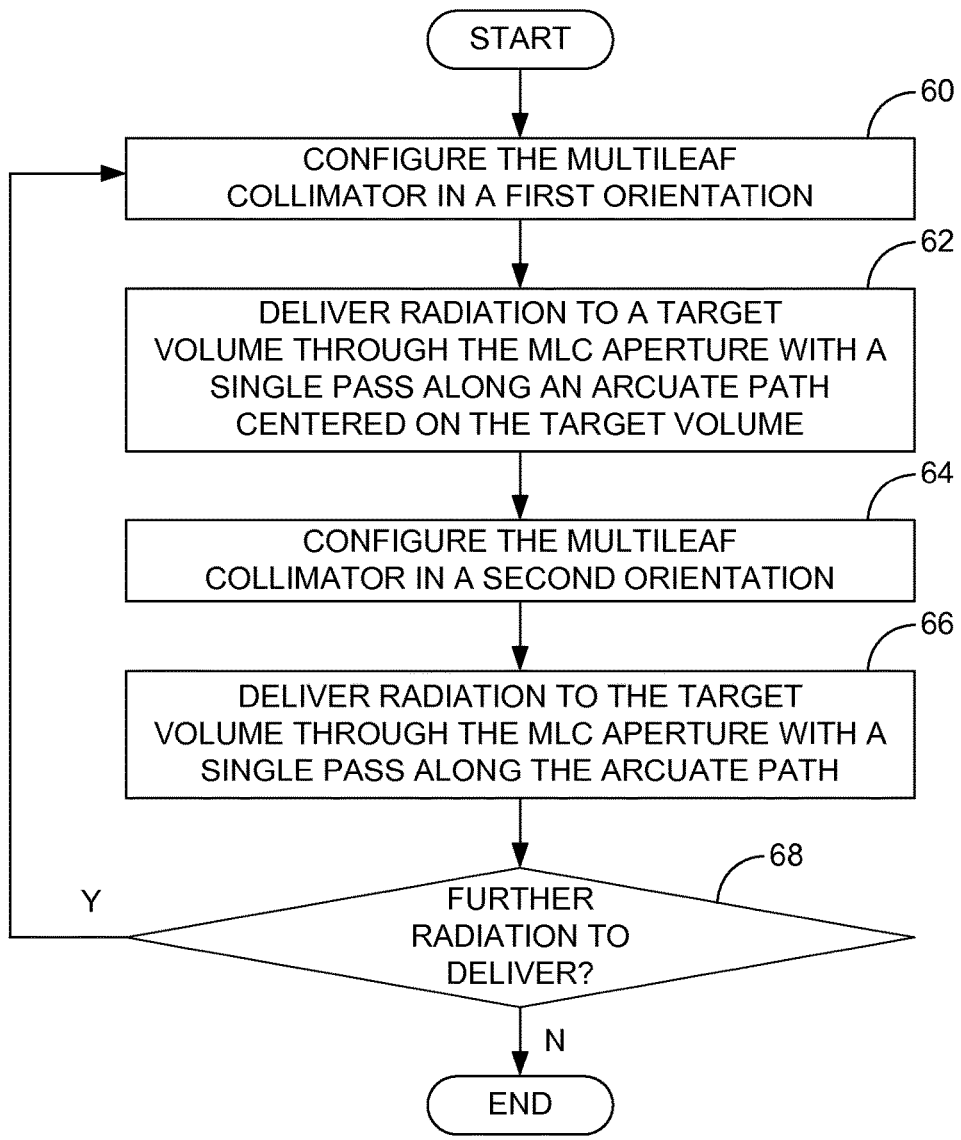
FIG. 4 is a flow diagram of an embodiment of a method for delivering radiation to a target volume within a patient.
Figure 5:
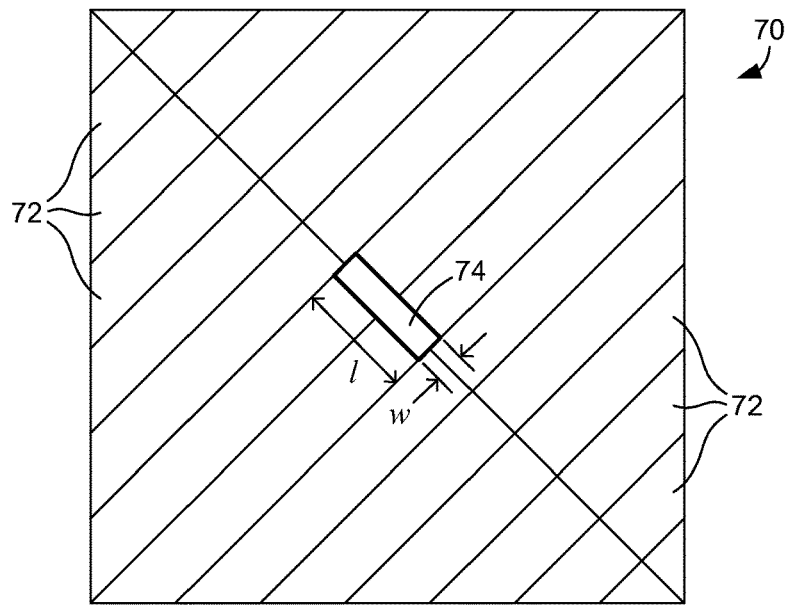
FIG. 5 is a partial schematic diagram of a multileaf collimator (MLC) of a radiation treatment machine, the collimator shown in a first configuration.

FIG. 4 illustrates a method for delivering radiation to a target volume with a radiation treatment machine in the above-described manner. Beginning with block 60 of this figure, MLC is configured in a first orientation. In cases in which the target volume is very small, the first orientation is in one in which the maximum resolution of the MLC is used. As described above, this is achieved when each opposed pair of leaves is closed except for the two center pairs of leaves. FIG. 5 illustrates such an orientation. As shown in this figure, an MLC 70 comprises multiple linearly displaceable leaves 72 that form opposed pairs of leaves that can be moved toward or away from each other. In the orientation of FIG. 5, the leaves 72 of each pairs have been brought into contact or near contact with each other so as form closed pairs but the two center pairs of opposed leaves, which are spaced from each other so as to be open and form a small rectangular aperture 74 having a width w that is defined by the distance between the ends of the leaves and a length/that is dictated by the width of the leaves (i.e., l is twice the width of the leaves). In the example of FIG. 5, the leaves 72 of the MLC 70, and therefore the aperture 74, are situated at a 45 degree angle relative to the table of the machine.

As can be appreciated from FIG. 5, the width of the aperture 74 can be adjusted to be as small as desired by moving the ends of the leaves 72 closer together. For very small target volumes, the width may be selected to be in the range of approximately 0.1 to 4 mm. Significantly, however, the length of the aperture 74 can be no smaller than the width of two adjacent leaves 72. Accordingly, the resolution of the MLC 70 is limited by the width of its leaves 72. The width of the leaves 72, and the resolution of the radiation treatment machine, depends upon the particular MLC 70 with which the machine is equipped. In many such machines, this width is no smaller than 2.5 mm, in which case the minimum length of the aperture is no smaller than 5 mm.

Figure 7:
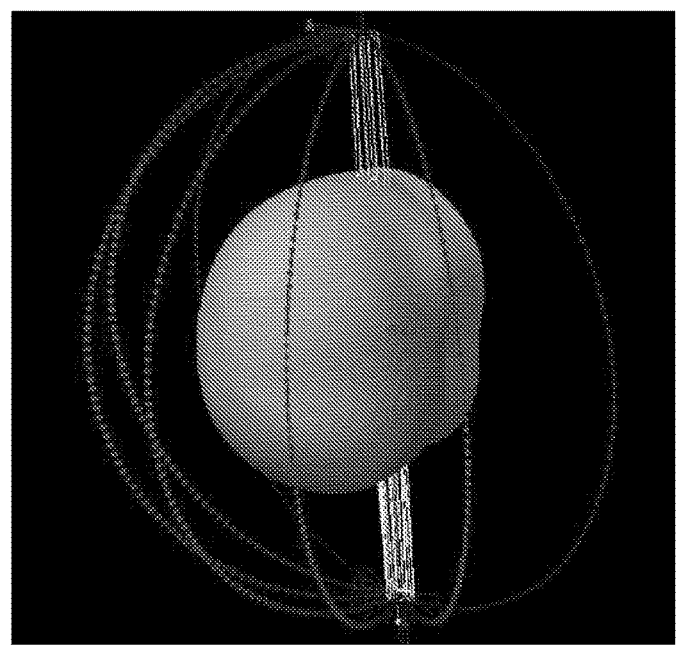
FIG. 7 is a computer model of a patient head illustrating arcuate paths traversed by a radiation source of a radiation treatment machine during radiation treatment.

With reference to FIG. 4 and block 62, once the MLC has been configured in the first orientation, radiation can be delivered to the target volume through the aperture with a single pass along an arcuate path centered on the target volume. In some embodiments, the radiation is delivered along the arcuate paths through rotation of the radiation treatment machine's gantry. FIG. 7 illustrates such radiation delivery. As shown in this figure, the target volume is located within the center of the head of a patient, which depicted as a spheroid mass in the center of the figure. The side of the mass nearest the observer represents the top right side of the head when the patient is lying on his or her back. Multiple arcuate paths are identified in FIG. 7 with dashed lines. These paths extend from a top end of a vertical line that passes through the head and the target volume to a bottom end of the vertical line. Therefore, during each pass of the gantry, the gantry, and the radiation source, is able to travel through 180 degrees from the 0 degree point at the top end of the line to the 180 degree point at the bottom end of the line.

As can be appreciated from the arcuate paths identified in FIG. 7, the paths are much closer to each other at the beginning and end of each path. The paths can therefore be said to overlap each other at those ends. Because delivery of the same radiation dose throughout the arcuate path would result in higher cumulative doses being administered at the top and bottom of the head, the dosage distribution can be controlled as a function of the angular position of the gantry and the radiation source. In some embodiments, the radiation dose can be weighted so as to be proportional to the sine of the angular position, such as in the following relation:

$$w(\theta) \propto \sin\theta \qquad \text{[Equation 1]}$$

where $w(\theta)$ is the weighting factor applied to the radiation dose and $\theta$ is the gantry angle. In cases in which the weighting factor is computed using Equation 1, the radiation dose would be at a minimum at the 0 and 180 degree positions and at a maximum at the 90 degree position. Although such a weighting function can be applied, it is noted that, alternatively or in addition, the radiation can be delivered along only a portion of the arcuate path that excludes the top and/or bottom ends of the paths (e.g., the first few and/or the last few degrees along the path) so as to reduce the radiation overlap.

Figure 6:
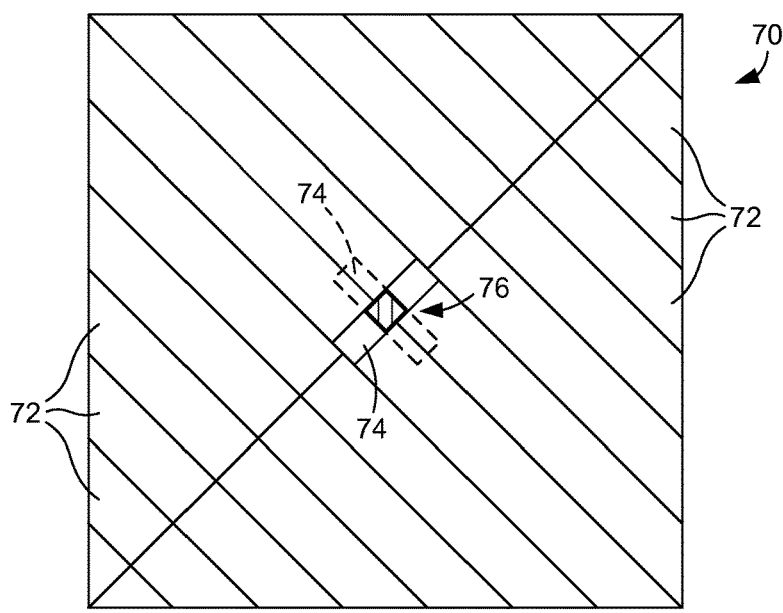
FIG. 6 is a partial schematic diagram of the MLC of FIG. 5 shown in a second configuration.

Once a single pass has been made along one of the arcuate paths with the MLC in the first orientation, the MLC can be configured in a second orientation, as indicated in block 64. FIG. 6 illustrates such an orientation. As shown in this figure, the MLC 70 has been rotated through 90 degrees such that the aperture 74 is angled 45 degrees in the opposite direction from that in FIG. 5. In this orientation, the aperture 74 is approximately 90 degrees out of phase with its orientation shown in FIG. 5 (that orientation is illustrated in FIG. 6 with dashed lines). As is apparent from FIG. 6, there is only a small rectangular (square) area 76 (identified with cross-hatching) at which the two apertures overlap each other. If the radiation is again delivered along the same arcuate path as was traversed with the MLC 70 in the configuration of FIG. 5, the cumulative result will be a relatively high (e.g., double) dose of radiation being emitted only through the "virtual aperture" represented by the area 76. As can be appreciated from FIG. 6, this area/virtual aperture 76 has a width and length that is only limited by the spacing of the leaves 72 and not the width of the leaves. Therefore, the virtual aperture 76 can have length dimensions that are much smaller than the smallest length dimensions of an actual aperture that can be physically produced by the MLC 70. In some embodiments, the virtual aperture 76 has both width and length dimensions that are greater than 0 mm but less than 5 mm. For example, the width and length dimensions can be in the range of approximately 0.1 to 4 mm. In such a case, relatively high radiation doses can be limited to very small target volumes, i.e., volumes much smaller than those that can be treated without forming the virtual aperture 76.

With reference back to FIG. 4 and block 66, once the MLC has been configured in the second orientation, radiation can be delivered to the target volume through the MLC aperture with another single pass along the same arcuate path identified in block 62. Accordingly a relative high dose of radiation is delivered along the arcuate path through the virtual aperture using the two passes identified in blocks 62 and 66.

Referring next to decision block 68, flow from this point depends upon whether or not further radiation is to be delivered to the patient. If not, flow for the session is terminated. If so, however, flow returns to block 60 and radiation is delivered to the patient in the same manner described above but along a different arcuate path. In some embodiments, radiation is delivered to the patient along approximately 5 to 10 180 degree arcuate paths with two passes being made along each path.

Figure 8:
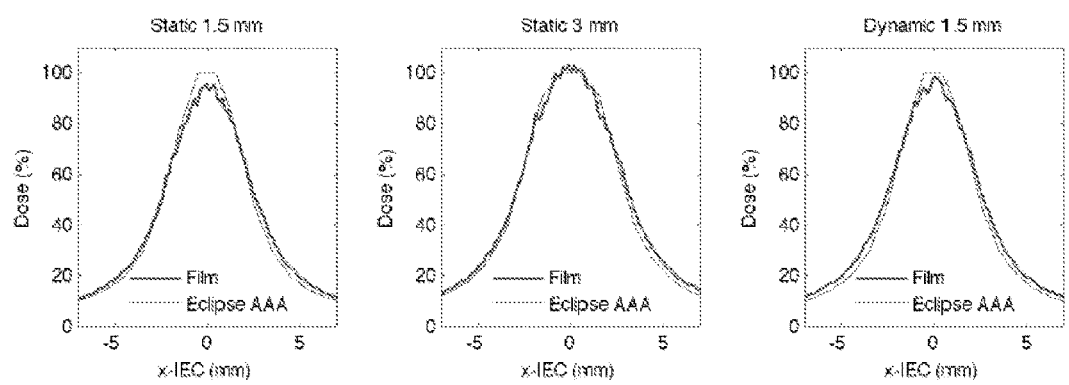
FIG. 8 includes graphs that show measured and calculated radiation dose profiles as a function of MLC aperture width.

FIG. 8 shows measured and calculated dose profiles for 1.5 mm and 3 mm leaf separations for two irradiation conditions. For the static condition, the patient support (treatment table) is stationary while the gantry rotates around the patient. After completing the arc delivery at each table position, the table is rotated. For the dynamic condition, the table and gantry rotate continuously.

The invention claimed is:

1. A method for providing radiotherapy treatment to a target volume of a patient, the method comprising:
    configuring a multileaf collimator of a radiation treatment machine in a first orientation so as to form an actual aperture having a first orientation;
    delivering radiation to the target volume through the actual aperture while in the first orientation with a single pass along an arcuate path centered on the target volume;
    configuring the multileaf collimator in a second orientation so as to place the actual aperture in a second orientation that is different from the first orientation; and
    delivering radiation to the target volume through the actual aperture while in the second orientation with a single pass back along the arcuate path such that a relatively large cumulative dose of radiation is delivered to the target volume through a virtual aperture created by an area of overlap between the first and second orientations of the actual aperture.

2. The method of claim 1, wherein configuring the multileaf collimator in the first orientation comprises positioning each pair of leaves of the multileaf collimator in a closed position with exception of a single pair of leaves that are spaced from each other, a space between the single pair of leaves defining a width of the actual aperture and a width of the single pair of leaves defining a length of the actual aperture.

3. The method of claim 2, wherein configuring the multileaf collimator in the second orientation comprises rotating the multileaf collimator through approximately 90 degrees.

4. The method of claim 3, wherein the actual aperture has a width of less than 5 mm and a length of at least 5 mm.

5. The method of claim 4, wherein the virtual aperture has a width and length that is less than 5 mm.

6. The method of claim 5, wherein the virtual aperture has a width and length that is in a range of approximately 0.1 to 4 mm.

7. The method of claim 1, wherein delivering radiation along the arcuate path comprises adjusting a radiation dose as a function of angular position along the arcuate path.

8. The method of claim 7, wherein adjusting the radiation comprises applying a weighting factor to the radiation dose.

9. The method of claim 8, wherein the weighting factor is a function of the sine of the angular position along the arcuate path.

10. A system for providing radiotherapy treatment to a target volume of a patient, the system comprising:
   a radiation treatment machine including a multileaf collimator having multiple pairs of opposed linearly displaceable leaves; and
   a computer that executes a radiotherapy treatment control program that is configured to control the radiation treatment machine so as to:
      configure the multileaf collimator in a first orientation so as to form an actual aperture having a first orientation,
      deliver radiation to the target volume through the actual aperture while in the first orientation with a single pass along an arcuate path centered on the target volume,
      configure the multileaf collimator in a second orientation so as to place the actual aperture in a second orientation that is different from the first orientation, and
      deliver radiation to the target volume through the actual aperture while in the second orientation with a single pass back along the arcuate path such that a relatively large cumulative dose of radiation is delivered to the target volume through a virtual aperture created by an area of overlap between the first and second orientations of the actual aperture.

11. The system of claim 10, wherein the radiation treatment machine comprises a linear accelerator.

12. The system of claim 10, wherein the first orientation is one in which each pair of leaves of the multileaf collimator in a closed position with exception of a single pair of leaves that are spaced from each other, a space between the single pair of leaves defining a width of the actual aperture and a width of the single pair of leaves defining a length of the actual aperture.

13. The system of claim 12, wherein the second orientation is in one in which the multileaf collimator and the actual aperture has been rotated through approximately 90 degrees relative to the first orientation.

14. The system of claim 13, wherein the actual aperture has a width of less than 5 mm and a length of at least 5 mm.

15. The system of claim 14, wherein the virtual aperture has a width and length that is less than 5 mm.

16. The system of claim 15, wherein the virtual aperture has a width and length that is in a range of approximately 0.1 to 4 mm.

17. The system of claim 10, wherein the radiotherapy treatment control program controls the radiation treatment machine to deliver radiation along the arcuate path in a manner in which a radiation dose varies as a function of angular position along the arcuate path.

18. The system of claim 17, wherein the radiation dose varies a function of the sine of the angular position along the arcuate path.

* * * * *